United States Patent [19]

Aubert et al.

[11] Patent Number: 5,597,558
[45] Date of Patent: Jan. 28, 1997

[54] USE OF EXTRACTS OF FILAMENTOUS BACTERIA AS COSMETIC AGENTS TO COMBAT AGEING OF THE SKIN

[75] Inventors: Lucien Aubert, Cap d'Ail; Richard Martin, Vouvray, both of France

[73] Assignee: L'Oreal, Paris, France

[21] Appl. No.: 437,546

[22] Filed: May 9, 1995

[30] Foreign Application Priority Data

May 10, 1994 [FR] France ................... 94 05741

[51] Int. Cl.⁶ ................ A61K 7/06; A61K 7/48
[52] U.S. Cl. .............. 424/70.1; 435/170; 514/844
[58] Field of Search .............. 435/170; 514/844; 424/70.1

[56] References Cited

U.S. PATENT DOCUMENTS 4,419,449  12/1983  Maillard ................... 435/170

FOREIGN PATENT DOCUMENTS 2283223  3/1976  France .
2693654  1/1994  France .
2034687  6/1980  United Kingdom .

OTHER PUBLICATIONS

S. Rivas Goday, "Physiography and Plant Landscape of Banos-de-Montemayor Caceres Spain", STN International Karlsruhe File Biosis, AN=76:226495 1975.

F. Grossi, "Riflessioni in tema di mezzi termali solfurei e dermatologia estetica", Clin. Ter., vol. 131, No. 6 1989, pp. 413–319.

R. Baudrimont, "Contribution a l'etude des Diatomees des sources sulfurees chlorurees sodiques mesothermales de Saint–Saveur", J. Med. Bord., vol. 144, No. 3, 1967, pp. 417–426.

*Primary Examiner*—C. Warren Ivy
*Assistant Examiner*—Evelyn Huang
*Attorney, Agent, or Firm*—Cushman Darby & Cushman Intellectual Property Group of Pillsbury Madison & Sutro LLP

[57] ABSTRACT

Use of extracts of filamentous bacteria in cosmetics.

According to the invention, an extract of at least one non-photosynthetic and non-fruiting filamentous bacterium is used as active ingredient for the preparation of a cosmetic composition intended to combat ageing of the skin.

Application in the treatment either of the skin for the purpose of reducing and/or of delaying the loss of elasticity, or of the scalp for the purpose of reducing and/or delaying greying of the hair.

7 Claims, No Drawings

USE OF EXTRACTS OF FILAMENTOUS BACTERIA AS COSMETIC AGENTS TO COMBAT AGEING OF THE SKIN

The present invention relates to the use of extracts of non-photosynthetic and non-fruiting filamentous bacteria as cosmetic agents to combat ageing of the skin.

It is known that ageing of the skin, whether due to age or to other factors such as environmental factors, is reflected in particular in a deterioration of the mechanical properties of the skin, and in particular a loss of elasticity and of tonicity, with the appearance of wrinkles. This phenomenon is particularly associated with an adverse change in the elastic tissues, and in particular a reduction in the number and diameter of the elastic fibres.

Ageing of the skin is also accompanied by a thinning out of all of the components of the skin, with a consequent increase in the fragility of the skin. The rarefaction of the fibroblasts and the impairment of their activity are considered to play a very important part in the skin ageing process.

It is also known that gaseous exchanges take place at the surface of the skin, with removal of carbon dioxide and absorption of oxygen. This phenomenon, known as breathing of the skin, decreases with age, and this decrease is considered to be a result of the decrease in epidermal activity.

It has now been discovered that extracts of non-photosynthetic and non-fruiting filamentous bacteria are capable of reducing and/or of delaying skin ageing when they are applied to the skin.

These extracts also have a stimulatory effect on melanocytes and are capable, when they are applied to the scalp, of reducing and/or of delaying greying of the hair, which may be considered as one of the consequences of ageing of the skin.

In the present Application, the expression "bacterial extracts" encompasses both actual extracts and the biomasses obtained after culturing bacteria. If desired, these biomasses may be at least partially dehydrated and/or ground. Obviously, the invention covers the use of extracts comprising any fraction of the biomass which possesses the same anti-skin-ageing properties as the whole biomass. The extracts used according to the invention also comprise derivatives obtained from the biomass, for example acylation derivatives.

The bacterial extracts of the invention are extracts of bacteria chosen from non-photosynthetic and non-fruiting filamentous bacteria as defined according to the classification of Bergey's Manual of Systematic Bacteriology, Vol. 3 Section 23, 9th ed., 1989.

Among these bacteria, there may more particularly be mentioned the bacteria belonging to the order Beggiatoales and especially the bacteria belonging to the genus Beggiatoa, for example such as various strains of *Beggiatoa alba* according to the definition given in Arch. Microbiol. (1984) 137, 139–144. It should be noted that this definition of *B. alba* corresponds to the former names *Beggiatoa arachnoidea, B. gigantea, B. leptomiformis, B. minima* and *B. mirabilis* of Bergey's Manual, 8th edition.

There may moreover be mentioned the bacteria belonging to the genus Vitreoscilla (which is known to be related to and often difficult to differentiate from the genus Beggiatoa), and also the bacteria belonging to the genus Flexithrix and the genus Leucothrix.

The bacteria which have just been-defined, and of which several have already been described, generally have an aquatic habitat and can be found especially in seawater or in thermal springs.

Among the bacteria which may be used, there may for example be mentioned:

*Vitreoscilla beggiatoïdes* (ATCC 43181),

*Beggiatoa alba* (ATCC 33555),

*Flexithrix dorotheae* (ATCC 23163),

*Leucothrix mucor* (ATCC 25107).

In order to-prepare the bacterial extract of the invention, it is possible to culture the said bacteria according to the known methods, and then to separate the biomass obtained. One preferred culturing process is that described in patent FR-269,654.

After culturing the bacteria, the biomass may be separated and isolated by various known methods, for example by filtration, by drying on a cylinder with a scraped prelayer, or centrifugation and/or freeze-drying. A prior concentration, for example at 80° C. under reduced pressure, can enhance this separation.

The bacterial extracts may be used in the form of derivatives, for example in the form of derivatives which are at least partially acylated. The acylation is carried out using a carboxylic anhydride or with a corresponding acyl chloride. Acetic anhydride or acetyl chloride may be used, for example. The acylation reaction is carried out so that at least some of the primary and secondary amine groups present in the bacterial biomass are acylated. The proportions of acylating agents and the conditions of the acylation reaction are readily determined by assaying, according to the standard methods (for example by potentiometry), the primary and secondary amine groups, before and after the acylation reaction.

In the compositions used according to the invention, the bacterial extracts are generally used in a proportion of from 0.01 to 2%, and particularly from 0.01 to 1% by dryweight of bacterial extract, relative to the weight of the composition.

These compositions contain the bacterial extract in the form of dispersions in a suitable vehicle such as, for example, water, organic solvents, fats, including oils, and mixtures thereof, especially emulsions.

They may in particular be in the form of aqueous-alcoholic or oleo-alcoholic lotions, gels, emulsions of liquid consistency, creams, solid sticks or vesicle dispersions. These compositions may be prepared according to the usual methods. They contain the ingredients and vehicles which enable them to be presented especially in one of the forms which have just been mentioned. They may additionally contain other active ingredients, for example such as ultraviolet-absorbing substances, hydrating agents, anti-free-radical agents, emollients and sequestering agents. They may also contain common ingredients such as preserving agents and fragrances.

In order to prepare compositions in the form, of vesicle dispersions using ionic or nonionic amphiphilic lipids, the process may be performed according to the known methods, for example by swelling the lipids in an aqueous solution in order to form spherules which are dispersed in the aqueous medium, as described in the article by Banghamet al., J. Mol. Biol.13, 238 (1965) or in patents FR-2,315,991 and 2,416,008. Other modes of preparing these vesicle dispersions are described in the work entitled "Les liposomes en biologie cellulaire et pharmacologie" [Liposomes in cell biology and pharmacology] Ed. INSERM/John Libbery Eurotext, 1987, pp. 6 to 18.

The subject of the invention moreover is a cosmetic treatment process for combatting ageing of the skin, characterized in that a bacterial extract as defined above is applied to the skin or the scalp, especially in the form of a composition as defined above.

The compositions are applied to the skin and/or the scalp according to the usual methods.

The examples which follow illustrate the invention without, however, limiting it.

EXAMPLE 1

Selection/adaptation-and culturing of a non-photosynthetic and non-fruiting filamentous bacterium The process was performed as described in Example 1 of FR-2,693,654.

The biomass is harvested by centrifugation.

The process is performed in an industrial type centrifuge, cooled to 20° C., which is capable of achieving an acceleration of greater than 5000×g.

The biomass thus obtained may be stabilized by heating (for example in an autoclave at 121° C. for 20 min), by drying, by freeze-drying or by freezing.

EXAMPLE 2

Preparation of an acetylated derivative 155 ml of 32% sodiumhydroxide solution are added to 100 g of dried bacterial biomass.

The mixture obtained is stirred at 4° C. for 2 hours. 117 ml of acetic anhydride are then added.

Freeze-drying is then carried out,

By assaying the primary and secondary amines, before and after acetylation, by potentiometry with perchloric acid, it is observed that about 60% of the primary and secondary amine groups of the starting material are acetylated.

In a similar manner, acetylated bacterial extracts were prepared starting with bacterial biomasses derived from cultures of Beggiatoa alba (ATCC 33555).

EXAMPLE 3

Cream

This cream corresponds to the following composition:

| | |
|---|---|
| Lyophilizate obtained in Example 1 | 0.05% |
| Carbomer 940* | 0.3% |
| Triethanolamine | 0.3% |
| Stearic acid | 3.0% |
| Cetyl alcohol | 2.0% |
| Auto-emulsifiable glyceryl monostearate | 3.0% |
| Soya oil | 10.0% |
| Lanolin alcohol | 2.0% |
| Isopropyl myristate | 4.0% |
| Cetyl and stearyl 2-ethylhexanoate | 4.0% |
| Perhydrosqualene | 3.0% |
| Paraffin | 2.0% |
| Glycerol | 3.0% |
| Preserving agents | 0.3% |
| Water qs | 100% |

*Carbomer 940: trade name denoting a crosslinked polyacrylic acid.

In order to prepare this cream, the aqueous phase containing the glycerol, the preserving agents and water is heated to 80° C.; the Carhomer 940 is dispersed therein, and this is then neutralized with triethanolamine. The fatty phase, heated and homogenized at 80° C. is introduced into the aqueous phase with vigorous stirring. The lyophilizate of Example 1 is dispersed in 10 g of water and introduced at 40° C. into the cream, with stirring. The mixture is cooled to room temperature.

This cream is applied to the skin of the face and the neck once or twice a day. After use for a sufficient period, it enables in particular a younger-looking skin to be obtained.

EXAMPLE 4

Milk for the skin

This milk has the following composition:

| | |
|---|---|
| Lyophilized acetylated derivative of Example 2 | 0.1% |
| Auto-emulsifiable glycerol monostearate | 3.0% |
| Petrolatum | 1.5% |
| Liquid petrolatum | 2.5% |
| Rice bran oil | 1.5% |
| Volatile silicone oil | 5.0% |
| Karite butter | 3.0% |
| Carbomer 940 | 0.2% |
| Triethanolamine | 0.2% |
| Xanthan gum | 0.1% |
| Glycerol | 3.0% |
| Fragrance | 0.1% |
| Preserving agents | 0.3% |
| Water qs | 100% |

This milk is prepared in a similar manner to that described in Example 3.

When applied to the skin of the face, this milk reduces the accelerated skin ageing effect observed in particular in individuals who expose themselves to the sun.

EXAMPLE 5

Composition to be applied to the scalp

These compositions are intended to delay the appearance of grey hair.

a) Gel

This gel has the following composition:

| | |
|---|---|
| Frozen suspension of Example containing 5% of active material | 1.0% |
| Carbomer 940 | 0.5% |
| Triethanolamine | 0.5% |
| Propylene glycol | 3.0% |
| Preserving agents | 0.3% |
| Ethanol | 28% |
| Water qs | 100% |

Daily application is advised.

b) Aqueous-alcoholic suspension

This suspension contains 0.5% of the lyophilized acetylated derivative obtained according to Example 2 in an ethanol-water mixture containing 35% by weight of ethanol.

EXAMPLE 6

Cream

An emulsion having the following composition was prepared according to the same procedure as in Example 3:

| | |
|---|---|
| Lyophilized acetylated derivative of Example 2 | 0.125% |
| Auto-emulsifiable base comprising: | |
|     Mineral oil | |
|     Petrolatum codex | |
|     Ozokerite | 20.000% |
|     Glycerol oleate | |
|     Liquid lanolin | |
| Liquid petrolatum codex | 5.000% |
| Glycerol | 5.000% |
| Aluminium stearate | 0.500% |
| Dipotassium EDTA | 0.050% |
| Magnesium sulphate | 0.700% |
| Preserving agents (methyl and propyl para-hydroxybenzoates) | 0.200% |
| Imidazolidinylurea (preserving agent) | 0.300% |
| Flagrance | 0.300% |
| Water qs | 100% |

Skin tolerance test

The process is performed according to the test of Marzulli and Maibach: the repeated application of a product or of a sensitizing substance in an occlusive dressing (in order to facilitate penetration) for a period of 3 weeks makes it possible, if the product is sensitizing, to induce the formation of specific antibodies.

After a rest period of 2 weeks, the product is reapplied (triggering test).

If there has been sensitization, an allergic reaction appears.

Procedure

The test was performed using the cream prepared above, on 50 volunteers, in the following way:

Materials

The product is applied under an occlusive dressing of brand name Leukotest in which the cotton compress receiving the test product is insulated from the hypoallergenic adhesive mass by a sheet of synthetic fibre and is bounded by a ring of cellophane which enables the skin reaction to be limited strictly to the test surface.

Application of the product

The patches are applied to healthy skin, without prior preparation.

The applications are repeated on the same site on the left shoulder of the volunteers, throughout the induction phase; the same area of skin thus theoretically receives 3 times per week, every other day, for three consecutive weeks, 0.1 ml of the product maintained under an occlusive dressing for 48 hours; the application is suspended until the triggering test as soon as a sign of intolerance is observed.

After a two-week rest period, a final application of the product is performed, both on the original site used for the induction (left shoulder), and on a new site defined on the right shoulder of each volunteer: the occlusive dressings are kept in place for 24 hours.

Examinations

During the induction phase

Before each application, the state of the skin is evaluated. This examination is repeated immediately after removal of the patches.

In the event of an inflammatory reaction, the applications of the product must be suspended, for the subject in question, until the triggering test.

During the triggering phase

The readings are taken immediately, and then 24 and 48 hours after removal of the patch.

These examinations allow observation:

during the first 9 applications on the same skin site, of any signs of intolerance by accumulation of the product;

after the triggering application, of any manifestations indicative of an allergic process.

Scale of evaluation

The clinician should assess the skin reaction according to the following scales:

Erythema:

0—absence of erythema

1—slight erythema

2—definite erythema

3—definite erythema with oedema

Pruritus:

0—absence of pruritus

1—mild pruritus

2—substantial pruritus

Eczematiform lesions:

0—absence of vesicles

1—presence of vesicles

The clinician will also make note of any comments from the volunteers.

Expression of results

The reactions to the product are evaluated according to:

a general criterion which takes account of the percentage of subjects having skin reactions, irrespective of the type;

a more specific criterion which takes account of the type of reactions observed and of their degree.

The following are defined by means of the above elements:

the magnitude of the irritant power, which is characterized by the appearance of reactions limited to erythema which may or may not be associated with oedema or with pruritus;

the magnitude of the sensitizing power, which is expressed by erythematous reactions, generally accompanied by pruritus, oedema and/or eczema, which are observed more particularly during the triggering phase.

Chronology of the test

The chronology of the applications is as follows:

| | |
|---|---|
| D 0 - | first application of patch for 48 hours |
| D 2 - | reading of the result and application of the 2nd patch |
| D 4 - | leading of the result and application of the 3rd patch |
| D 7 - | reading of the result and application of the 4th patch |
| D 9 - | reading of the result and application of the 5th patch |
| D 11 - | reading of the result and application of the 6th patch |
| D 14 - | reading of the result and application of the 7th patch |

| | |
|---|---|
| D 16 - | reading of the result and application of the 8th patch |
| D 18 - | reading of the result and application of the 9th patch |
| D 21 - | reading of the result |
| D 35 - | final application of the product under a patch for 24 hours |
| D 36 - | reading of the result ½ hour after removal of the patch |
| D 37 - | reading of the result 24 hours after removal of the patch |
| D38 - | reading of the result 48 hours after removal of the patch. |

Result

Induction phase

Out of 50 volunteers, no skin reaction was detected.

Triggering test

Out of 50 volunteers, no skin reaction was observed.

These results are particularly noteworthy given the presence, in the test cream, of preserving agents and of fragrance, for which the risks of potentiating the effects of sensitizing substances are well known.

EXAMPLE 7

Study of the skin respiration by the gas exchange method

The principle of the test consists in measuring the flow of oxygen and carbon dioxide crossing the epidermal barrier, in a given time, in subjects at rest.

To do this, a cell made of silicone resin, of cylindrical shape and circular cross-section, was made by moulding. The cell is applied by its open end to the skin of the forearm, and is kept in place using an elastic strap.

The test product (consisting of the lyophilizate of Example 1 at a concentration of 0.05%) is applied in an amount of 2 mg/cm$^2$.

The volume of air trapped within the cell thus placed in position is about 8.8 cm$^3$ and the area of skin in contact with the air thus imprisoned is 12.6 cm$^2$.

At time zero, two cells are attached simultaneously to the part to be studied, one covering a control area of skin, the other covering a treated area of skin.

A sample of 0.2 ml of air is withdrawn from the cell every 10 minutes using a gas syringe. The deformability of the cell makes it possible to maintain a constant pressure within it despite the volume of air withdrawn.

The air withdrawn is analysed by gas chromatography.

The test was performed on 16 individuals aged between 20 and 54 (average age 38).

An average increase of 27% in the flow of carbon dioxide and an increase of 21% in the flow of oxygen across the skin was observed for the zones of the treated skin, relative to the untreated control zones.

EXAMPLE 8

Effects on the proliferation of human skin fibroblasts

The fibroblasts are cultured in a complete nutrient medium, in an amount of 7,500 cells per well.

The test product is that of Example 2.

It is added to the cultures at various concentrations. The cells are then counted after varying periods of culturing.

It is observed, for example, that after 72 hours the number of cells treated with 50 µg/ml of the test product has increased by 30% relative to the number of cells in the control wells.

In the culture supernatants, the interleukin-1β, which is known to activate the elastin gene (which is the source of the skin's elasticity), was assayed by the ELISA technique.

In the case of the cells treated with a dose of 150 µg/ml, an IL-1β concentration of 34.5 pg/ml is found (control: 5.5 pg/ml).

Moreover, the search for elastase-type activity in the culture media (treated and control media) was negative.

EXAMPLE 9

Elastase inhibitory tests

The product used is that of Example 1 in lyophilized form.

The activity of a pancreatic elastase (Sigma; 83 U/mg; proteins; 15 mg/ml) is measured in the presence and in the absence of the test product.

For this, the elastase (diluted to 0.15 mg protein/ml) is added to the product supplemented with a triethanolamine solution (Triton X100).

A 38% reduction in the elastase activity is observed.

When the test product is diluted by half, the reduction in elastase activity is 31%.

EXAMPLE 10

Application tests on volunteers over one month

The test product is applied in the form of a cream at a concentration of 0.05% of active product. This cream has the formulation described in Example 3.

2 mg of the test product per square centimeter of skin are applied once a day to the skin of the face and of the forearms. The application lasts for four weeks.

The treatment was carried out on seventeen volunteers.

1.) Measurement of the mechanical properties of the epidermis

The biomechanical properties of the epidermis (extensibility Ue, tonicity Ur, elasticity Ur/Ue) are measured according to the method described by C. Escoffier et al. J. Invest. Dermatol. 93 : 353–357 (1989), with the apparatus described by Rigal and Lévêque, Bioeng. Skin 1: 13–23 (1985).

The measurements are made on the skin of the forearm by attaching the measuring probe to the skin using an adhesive.

The measurements were taken at time zero, and after two weeks and four weeks.

As regards the extensibility Ue, a 23% increase was noted after two weeks (30% at four weeks). For the tonicity Ur, the increase is 40% in the same time (43% at four weeks).

This shows that the product applied enhances the biomechanical properties of the epidermis, and in particular the elasticity, in an appreciable manner, even after two weeks of treatment.

2.) Effect on wrinkles

The effect on wrinkles was studied by image analysis. The method consists in illuminating the negative replica (silicone imprint of the wrinkles in the region close to the eyelids referred to as the "crow's feet") using an oblique light which causes shadows to be thrown behind each wrinkle. These shadows are quantified by image analysis according to the method described by Corcuff et al., J. of the Soc. of Cosmet. Chem. 34, 177–190 (1983) and by Corcuff, Acta Stereologica 2(1) 85–88 (1983).

This method enables the surface area of the wrinkles studied to be measured. It was found that the surface area of the wrinkles is significantly reduced-after four weeks. In parallel, a reduction in the number of wrinkles measuring between 1 and 9 mm in length is noted, as well as a reduction in the average length of wrinkles shorter than 1 mm in length.

3.) Thickness of the skin

The effects on the thickness of the skin of the forearm was also evaluated in the method known as the skin fold measurement (reference: Dykes et al., Arch. Dermatol. Res. 256–261, 1976), using a pincer fitted with a graduated dial, available from Schnelltaster. The thickness of the skin held between the two jaws of the pincer is read directly off the dial.

A significant increase of 2% is observed after two weeks, and of 3.5% after four weeks of treatment.

We claim:

1. A cosmetic treatment process to combat ageing of the skin comprising applying an extract of at least one non-photosynthetic and non-fruiting filamentous bacterium of the order Beggiatoales to the skin or scalp of a person in need of at least one of: enhancing the elasticity and tonicity of the skin, reducing the number and length of wrinkles of the skin, reducing the thinning of the skin due to ageing, stimulating the proliferation of fibroblasts of human skin, stimulating melanocytes, reducing greying of the hair, delaying greying of the hair, or increasing skin respiration.

2. The process of claim 1 wherein said extract is an acylated derivative of said extract.

3. The process according to claim 1 wherein said bacterium belongs to the genus Beggiatoa, Vitreoscilla, Flexithrix or Leucothrix.

4. The process according to claim 1 wherein said bacterium is a *Beggiatoa alba* strain.

5. The process according to claim 1 wherein said extract consists of the bacterial biomass obtained from culturing said bacterium and said biomass is at least partially dehydrated, freeze-dried or ground.

6. The process according to claim 1 wherein said extract is applied in the form of a composition containing a proportion of from 0.01 to 2% by weight of said composition.

7. The process according to claim 6 wherein said proportion is from 0.01 to 1% by weight.

* * * * *